US009652965B2

(12) United States Patent
Sadhu (10) Patent No.: US 9,652,965 B2
(45) Date of Patent: May 16, 2017

(54) SYSTEM AND METHOD FOR TRANSMITTING ALERTS AND NOTIFICATIONS TO A USER

(71) Applicant: Rajendra Padma Sadhu, Somerset, NJ (US)

(72) Inventor: Rajendra Padma Sadhu, Somerset, NJ (US)

( * ) Notice: Subject to any disclaimer, the term of this patent is extended or adjusted under 35 U.S.C. 154(b) by 561 days.

(21) Appl. No.: 14/041,880

(22) Filed: Sep. 30, 2013

(65) Prior Publication Data

US 2014/0028456 A1  Jan. 30, 2014

Related U.S. Application Data

(63) Continuation-in-part of application No. 13/105,925, filed on May 12, 2011, now Pat. No. 8,568,313, which is a continuation-in-part of application No. 12/722,554, filed on Mar. 12, 2010, now abandoned.

(51) Int. Cl.
| | |
|---|---|
| *G08B 1/08* | (2006.01) |
| *G08B 21/18* | (2006.01) |
| *A61B 5/00* | (2006.01) |
| *G01S 19/17* | (2010.01) |
| *G08B 21/04* | (2006.01) |
| *A61B 5/11* | (2006.01) |
| *G08B 25/00* | (2006.01) |
| *G01S 19/39* | (2010.01) |

(52) U.S. Cl.
CPC .......... *G08B 21/18* (2013.01); *A61B 5/1112* (2013.01); *A61B 5/681* (2013.01); *A61B 5/7465* (2013.01); *G01S 19/17* (2013.01); *G08B 21/0453* (2013.01); *G08B 25/005* (2013.01); *A61B 5/0022* (2013.01); *G01S 19/39* (2013.01)

(58) Field of Classification Search
None
See application file for complete search history.

(56) References Cited

U.S. PATENT DOCUMENTS

| | | | |
|---|---|---|---|
| 2011/0148626 A1* | 6/2011 | Acevedo | G01S 5/0027 340/539.13 |
| 2012/0232961 A1* | 9/2012 | Wellman | G05D 1/0282 705/7.38 |
| 2013/0040661 A1* | 2/2013 | Grube | H04L 12/1895 455/456.3 |

(Continued)

*Primary Examiner* — Julie Lieu
(74) *Attorney, Agent, or Firm* — Maier & Maier, PLLC (57) ABSTRACT

A system for transmitting alerts and notifications to a user. The system includes a user wearable portable data communication unit configured to set a predetermined period of time and select a geographical area by using a mapping software integrated with the user wearable portable data communication unit for geo-fencing the selected geographical area, an alerting unit configured in the user wearable portable data communication unit to transmit notifications and alerts to predefined list of contacts on determining the crossing of the user from the selected geo-fence area and exceeding the predetermined time period set by the user and a web based server unit in communication with user wearable portable data communication unit through a data communication network configured to store the predefined list of contacts, threshold levels, frequency, way points, current location of the user and software versions.

8 Claims, 5 Drawing Sheets

(56) References Cited

U.S. PATENT DOCUMENTS

| | | | |
|---|---|---|---|
| 2014/0022050 A1* | 1/2014 | Dua | H04W 64/003 340/5.2 |
| 2014/0070950 A1* | 3/2014 | Snodgrass | G06F 19/327 340/573.5 |
| 2014/0120977 A1* | 5/2014 | Amis | H04W 4/22 455/521 |
| 2014/0218192 A1* | 8/2014 | Riggins | G06Q 10/10 340/539.13 |
| 2014/0323104 A1* | 10/2014 | Derrick | G07C 1/20 455/414.1 |
| 2014/0368601 A1* | 12/2014 | deCharms | H04W 4/021 348/14.02 |
| 2015/0022365 A1* | 1/2015 | Warren | G08B 25/10 340/687 |
| 2015/0215758 A1* | 7/2015 | Hymowitz | H04W 4/22 455/404.2 |
| 2015/0288797 A1* | 10/2015 | Vincent | H04M 1/72538 455/404.2 |
| 2015/0332573 A1* | 11/2015 | Selmanovic | H04L 67/1095 455/457 |
| 2016/0029155 A1* | 1/2016 | Kerr | H04W 4/02 455/456.3 |

\* cited by examiner

SYSTEM AND METHOD FOR TRANSMITTING ALERTS AND NOTIFICATIONS TO A USER

TECHNICAL FIELD

The present disclosure generally relates to a user wearable portable data communication device. More particularly, the present disclosure relates to system and method for transmitting alerts and notifications to a user.

BACKGROUND

Conventionally, devices such as fitness watches, heart rate monitors, GPS-enabled fitness monitors, health monitors (e.g., diabetic blood sugar testing units), digital voice recorders, pedometers, altimeters, and other conventional personal data capture devices are generally manufactured for conditions that occur in a single or small groupings of activities. Problematically, though, conventional devices do not provide effective solutions to users in terms of providing a comprehensive view of one's overall health or wellness as a result of a combined analysis of data gathered. This is a limiting aspect of the commercial attraction of the various types of conventional devices listed above, generally, if the number of activities performed by conventional personal data capture devices increases, there is a corresponding rise in design and manufacturing requirements those results in significant consumer expense, which eventually becomes prohibitive to both investment and commercialization.

Further, often times people purchases diagnostic devices with sensors either in patch format or body worn or stand alone or fixed format and do not use them due to the monthly subscription costs thus making it a difficult value proposition for reducing the churn rates and for patient engagement/customer retention to effectively provide service to the customer, thus rewarding the user based on the usage and providing cash incentives based on the usage will lead to higher customer retention and patient engagement for the betterment of health. Customer can get rewards from providers like insurance companies, monitoring companies, hospitals, pharmacies based on these rewards; this automatic and continuous data from the user through the wearable device from the sensors will provide a value add to both the customer and provider.

Moreover, these body worn devices may also include an impact-responsive stopwatch, which is designed to enable a person taking part in a sport to measure and record time without a risk of a violent fall, and which is used in such a manner that the user gives an impact to the stopwatch by a striking action or the like to record or hold a split time at an intermediate point and to stop timing at a goal point. There is a possibility of the stopwatch receiving impacts from various causes whilst doing a sport. For example, in a case where an impact-responsive stopwatch of this kind is used in a skiing downhill race, an impact caused by violent stock work or striking against a pole may result in recording of an erroneous split time or termination of timing before the actual goal point is reached due to misidentification of an intermediate point as a goal point may occur. Thus, it is difficult to perform timing in accordance with one's intention.

Conventionally, a battery operated panic alarm wristwatch having a watch and a band, and audio transducer for producing an audio signal. A magnetic switch for activating the battery is disposed in the band and a hook and loop fastener is used for keeping the band closed. The use of hook and loop fasteners makes it easy to "yank off" the watchband during an attack, such that when the watchband is opened, a switch is closed and an alarm sounds. However, by its very nature, such a device does not maintain the activated alarm with the wearer, in order to attract attention to the wearer. Further, a personal security alarm combined with a wristwatch including a single exposed activation button on a large surface thereof, to be easily activated by a person's finger or face; a reset button is hidden on the underside of the device to require removal of a buckle fastener before resetting can be done. Thus the wristwatch, band or any body worn device is not used for transmitting notifications or alerts to the predefined users based on the geographical location.

Furthermore there will be many instances where a user need to be notified to exit out of defined area within a span of time for safety and security purposes, ignoring this could be life threatening too, when such instances happen friends, relatives, first responders and care givers need to be alerted immediately, there is no such system or device exists to help in these circumstances.

Often times when there is an application software change to the system, user has to update manually upgrade by connecting through wired or wireless and manually initiating the device software upgrade. This could be tedious and time taking, lack of real-time configuration updates are the key when it's the matter of user safety and security.

Manufacturers often forget considering the visually and hearing impaired users when certain features are introduced into a device which are very valuable for these target customers. By making small changes to the offerings they produce tremendous benefit to these target customers.

In the light of aforementioned discussion there exists a need of a system and method for transmitting alerts and notifications to a user wearing a user wearable portable data communication unit.

BRIEF SUMMARY

The following presents a simplified summary of the disclosure in order to provide a basic understanding to the reader. This summary is not an extensive overview of the disclosure and it does not identify key/critical elements of the disclosure or delineate the scope of the disclosure. Its sole purpose is to present some concepts disclosed herein in a simplified form as a prelude to the more detailed description that is presented later.

A more complete appreciation of the present disclosure and the scope thereof can be obtained from the accompanying drawings which are briefly summarized below and the following detailed description of the presently preferred embodiments.

Exemplary embodiments of the present disclosure are directed towards a system for transmitting alerts and notifications to a user. According to a first aspect, the system includes a user wearable portable data communication unit configured to set a predetermined period of time and select a geographical area by using a mapping software integrated with the user wearable portable data communication unit for geo-fencing the selected geographical area.

According to the first aspect, the system includes an alerting unit configured in the user wearable portable data communication unit determines the crossing of the user wearing the user wearable portable data communication unit from the selected geo-fence area and exceeding the predetermined time period set by the user to transmit notifications and alerts to predefined list of contacts and to the corresponding user wearing the user wearable portable data communication unit. The notifications, alerts and indications are transmitted to the predefined list of contacts on determining the current geographical location of the user in accordance with the predetermined time period set to the user wearable portable data communication unit.

According to the first aspect, the system includes a web based server unit in communication with user wearable portable data communication unit through a data communication network configured to store at least one of predefined list of contacts; threshold levels, frequency, way points, current location of the user and software versions to update the user wearable portable data communication unit with the latest settings. The latest settings comprising global positioning system sampling interval and data upload interval.

According to the first aspect, the system includes a display unit configured in the user wearable portable data communication unit to display the geographical area selected by the user through mapping software integrated with the user wearable portable data communication unit.

According to a second aspect, a method for transmitting alerts and notifications to a user is disclosed. According to the second aspect, the method includes setting a predetermined period of time to a user wearable portable data communication unit by a user and selecting a geographical area displayed over the user wearable portable data communication unit by using a mapping software. The mapping software integrated with the user wearable portable data communication unit configured to fence the selected geographical area.

According to the second aspect, the method includes transmitting notifications to predefined list of contacts provided by the user wearing the user wearable portable data communication unit by an alert unit on determining crossing of the user wearing the user wearable portable data communication unit from the selected geo-fence area and exceeding the predetermined time period set by the user.

According to the second aspect, the method includes prompting safety response alerts to the user wearing the user wearable potable data communication unit based on the predetermined time period set by the user and the alerts comprising an alert message and an alarm sound.

According to the second aspect, the method includes dynamically responding back to the prompted alerts transmitted to the user wearable portable data communication unit for avoiding the transmission of notifications to the predefined list of contacts provided by the user.

According to the second aspect, the method includes at least one of polling a web based server unit by the user wearable portable data communication unit through a data communication network for receiving the automatic trigger from the web based server unit, latest firmware version and the updated versions of firmware stored in the web based server unit.

According to the second aspect, the method includes storing the updated settings received from the web based server unit in a memory unit configured in the user wearable portable data communication unit to act in accordance with the stored settings. The method also includes storing the predefined list of contacts, threshold levels, frequency, way points, current location of the user and software versions in the web based server unit communicating with the user wearable portable data communication unit.

According to the second aspect, the method includes collecting a prime location contiguous to the current geographical location of the user wearable portable data communication unit by the mapping software based on the current global positioning system of the user wearable portable data communication unit. Further, the collected one or more prime locations contiguous to the current geographical location of the user wearable portable data communication unit are transmitted to the user wearable portable data communication unit worn by a visually impaired person through a speaker, Bluetooth and radio communication according to a predetermined time period set by the user.

BRIEF DESCRIPTION OF DRAWINGS

Other objects and advantages of the present disclosure will become apparent to those skilled in the art upon reading the following detailed description of the preferred embodiments, in conjunction with the accompanying drawings, wherein like reference numerals have been used to designate like elements, and wherein.

DETAIL DESCRIPTION

It is to be understood that the present disclosure is not limited in its application to the details of construction and the arrangement of components set forth in the following description or illustrated in the drawings. The present disclosure is capable of other embodiments and of being practised or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

Figure 1:
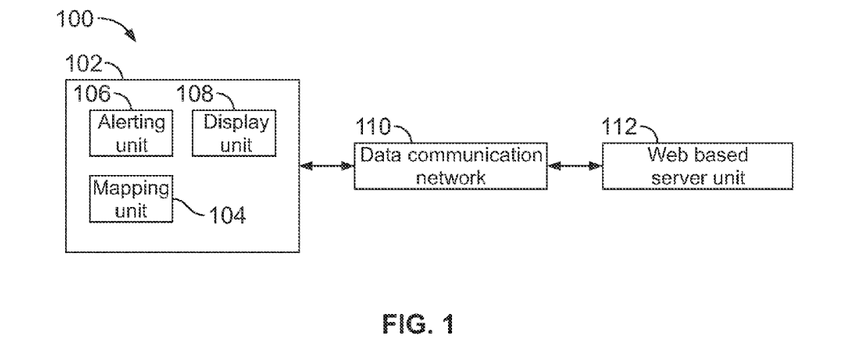
FIG. 1 illustrates a block diagram of a system for transmitting alerts and notifications to a user.

FIG. 1 illustrates a block diagram 100 of a system for transmitting alerts and notifications to a user. The system 100 includes a user wearable portable data communication unit 102 communicating with a web based server unit 112 through a data communication network 110. The user wearable portable data communication unit 102 may include but not limited to a hand watch, a wrist band, a band and the like worn as a strap or band around an arm, leg, ankle or any other bodily appendage or feature. Further, the user wearable portable data communication unit 102 includes a mapping unit 104 which includes a software program either standalone or coupled with hardware components which may include but not limited to displaying or relaying the voice, an alert unit 106 which includes a software program either standalone or coupled with hardware components which may include but not limited to displaying as a message on the device or relaying the voice, and a display unit 108 which includes a software program and a hardware component. For convenience, the system 100 discloses only about the unique user wearable portable data communication unit 102 communicating with the web based server unit 112. However it should be understood that in practise there may be any number of user wearable portable data communication units as similar as the present disclosed user wearable portable data communication unit 102 and a cluster of web servers used to establish a communication with the multiple number of user wearable portable data communication units, which can be included in the system. Therefore the present disclosure is not limited in the number of user wearable portable data communication units or number of web server units that may be included and/or supported by the system with the disclosed embodiments.

As shown in FIG. 1, the user is enabled to select a geographical area by using mapping unit 104 integrated within the user wearing the user wearable portable data communication unit 102 for geo-fencing the selected geographical area. The mapping unit 104 integrated within the corresponding user wearable portable data communication unit 102 is enabled to communicate with the web based server unit 112 for accessing the data and configuration and the like. The selected geographical area is either displayed over the display unit 108 integrated within the user wearable portable data communication unit 102 or blocked from displaying depending on the user preferences. The user is also further enabled to set a predetermined period of time to the user wearing the user wearable portable data communication unit 102 before entering the specific geo-fence area selected by the user. The user wearable portable data communication unit 102 worn by the user acts as a stop watch after entering the specified geo-fence area and transmits notifications and alerts to the user, if the set time period exceeds or if the user crosses the specified geo-fence area or between a set period of time.

As further shown in FIG. 1, if the user wearing the user wearable portable data communication unit 102 crosses the specified geo-fence area or exceeds the predetermined time period set by the user, the notifications and alerts are transmitted to the predefined list of contacts provided by the user by using an alerting unit 106 integrated within the user wearable portable data communication unit 102. The notifications and alerts transmitted to the predefined list of contacts may include but not limited to short messaging service, emails, voice mails and the like. Also further, the user wearing the corresponding user wearable portable data communication unit 102 is also used as a safety device by setting a predetermined safety response back alarm, which is used to prompt the user with short messages like but not limited to "are you safe" for every few minutes in accordance with the time period set by the user in the user wearable portable data communication unit 102 which may include but not limited to a watch, portal device and the like. The prompting alert generated by the user wearable portable data communication unit 102 to be dynamically responded back by pressing a button configured in the user wearable portable data communication unit 102 to indicate that the user is safe. If there is a lack of response from the user, the user wearable portable data communication unit 102 transmits the notifications to the predefined list of contacts provided by the user. Also, the user will have an ability to cancel the alerts if allowed.

Moreover, the web based server unit 112 in communication with the user wearing the user wearable portable data communication unit 102 through a data communication network 110 is used to store the predefined list of contacts provided by the corresponding user wearable portable data communication unit 102. The web based server unit 112 is also enabled to upload the predetermined threshold levels, frequency, way points and current location of the user provided by the corresponding user wearable portable data communication unit 102. Further the web based server unit 112 is also used to store the network name of the user wearable portable data communication unit 102, packet size and the software versions, user data, custom configuration settings. The user wearable portable data communication unit 102 communicating with the web based server unit 112 frequently polls the web based server unit 112 for updating the user wearable portable data communication unit 102 with the latest updates of software versions stored in the web based server unit 112. The latest updated software settings made in the user wearable portable data communication unit 102 may include but not limited to global positioning system sampling interval and data upload interval and the like received by the web based server unit 112 are stored in a memory integrated within the user wearable portable data communication unit 102. The web based server unit 112 could be individual server or a cluster of web servers which may include but not limited to one to n number of web based server units depending on the usage of servers by the users. The data communication network 110 used to establish a communication between the user wearable portable data communication unit 102 and the web based server unit 112 may include but not limited to a http based application layer, https application layer, user datagram protocols, transmission control protocols or internet protocols and the like.

Furthermore, the user wearing the user wearable portable data communication unit 102 is enabled to transmit the current global positioning system of the corresponding user wearable portable data communication unit 102 for collecting the contiguous prime locations by hitting the maps application programming interface (API) included in the mapping software 104. The collected contiguous prime locations are transmitted to the corresponding user wearable portable data communication unit 102. If the user wearing the corresponding user wearable portable data communication unit 102 is a visually impaired person, the data received by the user wearable portable data communication unit 102 is conveyed to the corresponding user through a speaker, Bluetooth, radio and the like. The data received by the user wearable portable data communication unit 102 may include but not limited to the notifications, alerts, contiguous prime locations, deals at the nearby stores, way points, turn by turn directions and the like.

Figure 2:
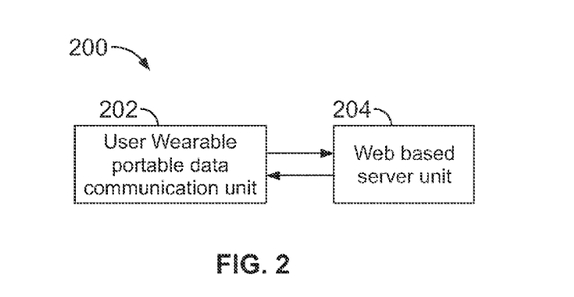
FIG. 2 is a diagram depicting a communication established between a user wearable portable data communication unit and a web based server unit.

FIG. 2 is a diagram 200 depicting a communication established between a user wearable portable data communication unit and a web based server unit. The web based server unit 204 is polled by a user wearable portable data communication unit 202 through a data communication network for verifying the availability of latest firmware versions and download the respective firmware version found to be different from the present version used in the user wearable portable data communication unit 202. The web based server unit 204 receiving a request from the user wearable portable data communication unit 202 generates an automatic trigger to indicate the availability of latest firmware versions or update versions of firmware by transmitting a user datagram protocol or a short message service or a flag in hypertext transfer protocol (http) as a response to a user wearable portable data communication unit 202. The flag in http response is obtained by posting the data which may include but not limited to data collected by the global positioning system or a sensor and the like integrated with the user wearable portable data communication unit 202, which triggers a firmware to download or install or plain a settings update for loading over the user wearable portable data communication unit 202.

Figure 3:
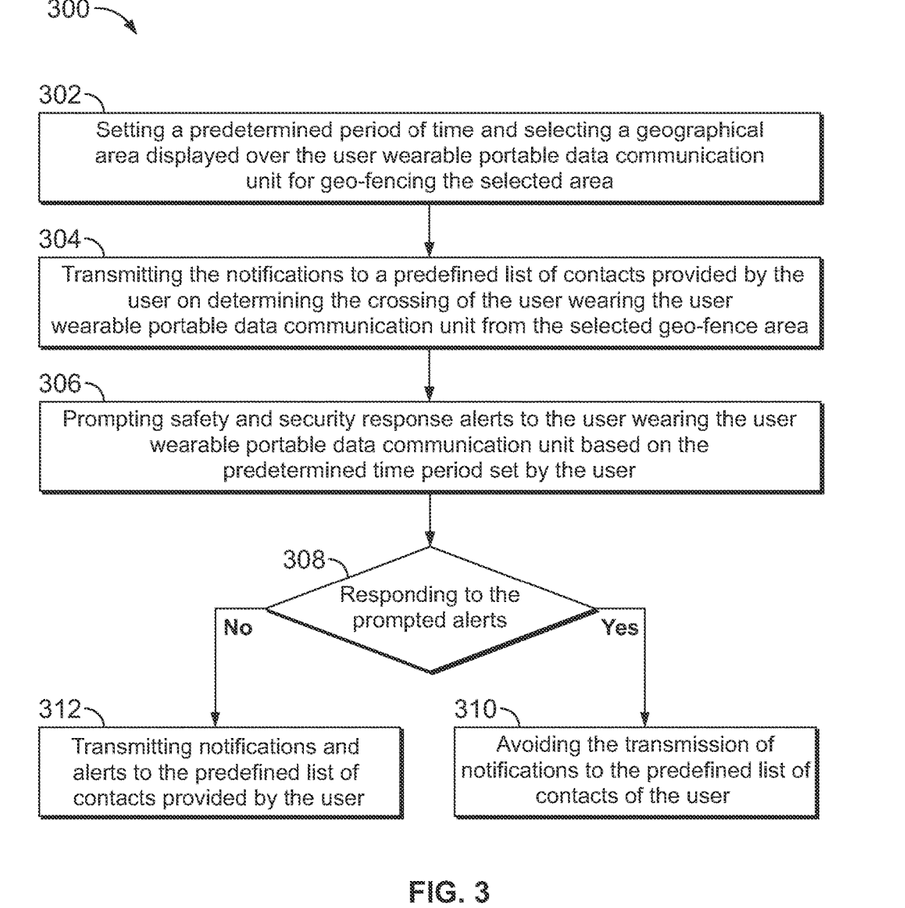
FIG. 3 is a flow diagram illustrating a method for transmitting alerts and notifications to a user.

FIG. 3 is a flow diagram 300 illustrating a method for transmitting alerts and notifications to a user. According to a non limiting exemplary embodiment of the present disclosure, the method for transmitting alerts and notifications to a user starts at step 302 by setting a predetermined period of time to a user wearing the user wearable portable data communication unit and selecting a geographical area displayed over the user wearable portable data communication unit for geo-fencing the selected area. Next at step 304, if the user wearing the user wearable portable data communication unit crosses the selected geo-fence area or exceeds the predetermined time period set by the user a notification is transmitted to a predefined list of contacts of the user stored in the web based server unit.

Further, at 306 the user wearing the user wearable portable data communication unit configured to receive a prompted safety and security response alerts based on the predetermined time period set by the user. At 308 the response to the prompted alerts is determined, if the response is generated by the user wearing the user wearable portable data communication unit the method continues with 310 by avoiding the transmission of notifications to the predefined list of contacts provided by the user. Further, if there is lack of response from the user at 308, the method continues with step 312 by transmitting notifications and alerts to the predefined list of contacts provided by the user.

Figure 4:
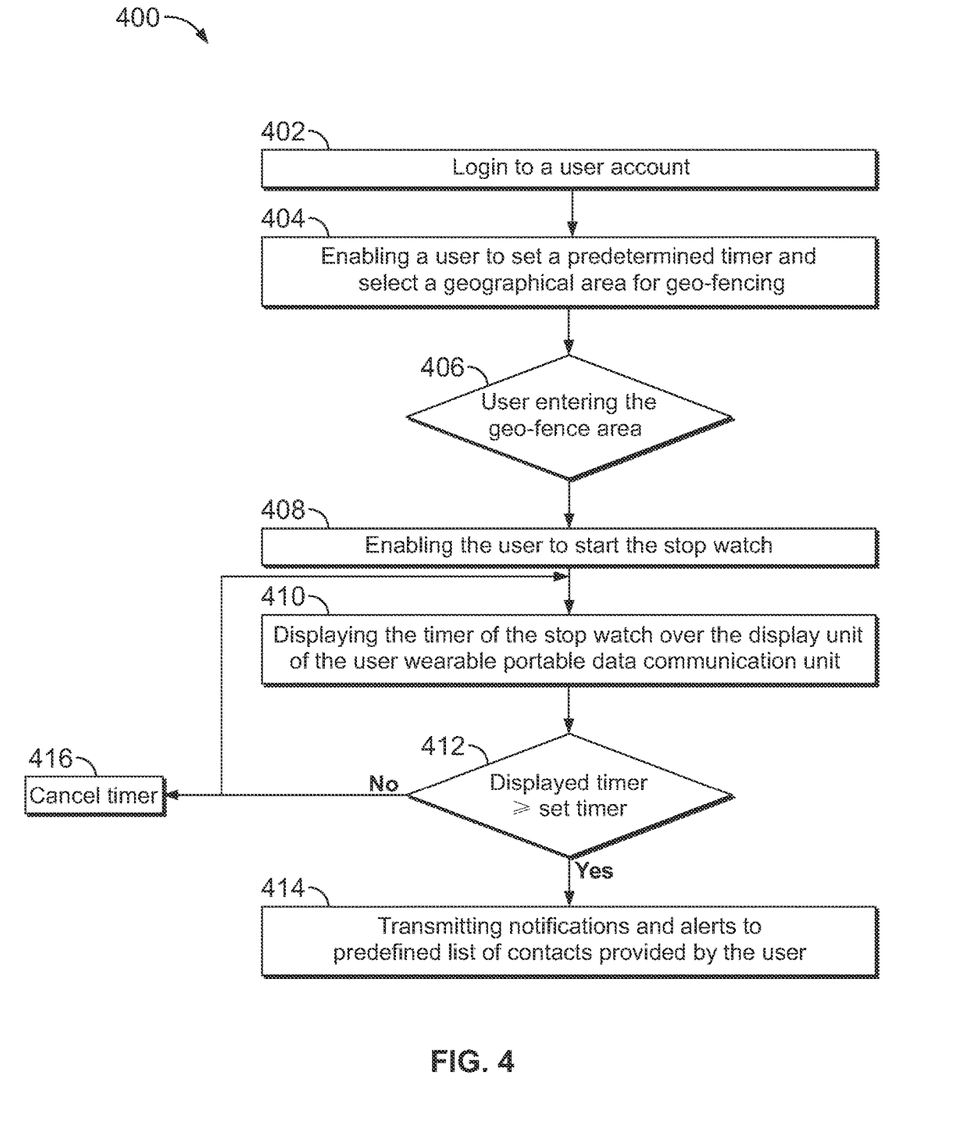
FIG. 4 is a flow diagram illustrating the process of transmitting notifications to a user based on the predetermined time.

FIG. 4 is a flow diagram 400 illustrating the process of transmitting notifications to a user based on the predetermined time. According to a non limiting exemplary embodiment of the present disclosure, at 402 the user wearing the user wearable portable data communication unit logins to his/her registered user account through a web based server unit over a portable device or through an application downloaded on the user wearable portable data communication unit. Next at 404 the user is enabled to set a predetermined timer and select a geographical area for geo-fencing the selected area. Further, when the user enters the geo-fence area at 406, the user is enabled to start the user wearable portable data communication unit referred as stop watch at 408.

Further, at 410 the readings of the stop watch including seconds and milliseconds are displayed over the display unit integrated within the user wearable portable data communication unit. Next at 412 the displayed time is compared with the predetermined set timer as whether the displayed time is greater than or equal to set timer. If the displayed time is found to be greater than or equal to set time, the method continues with 414 by transmitting notifications and alerts to the predefined list of contacts provided by the user and if the displayed time is found to be less than the set time, the method continues with 416 by cancelling the timer and further continues with 410.

Figure 5:
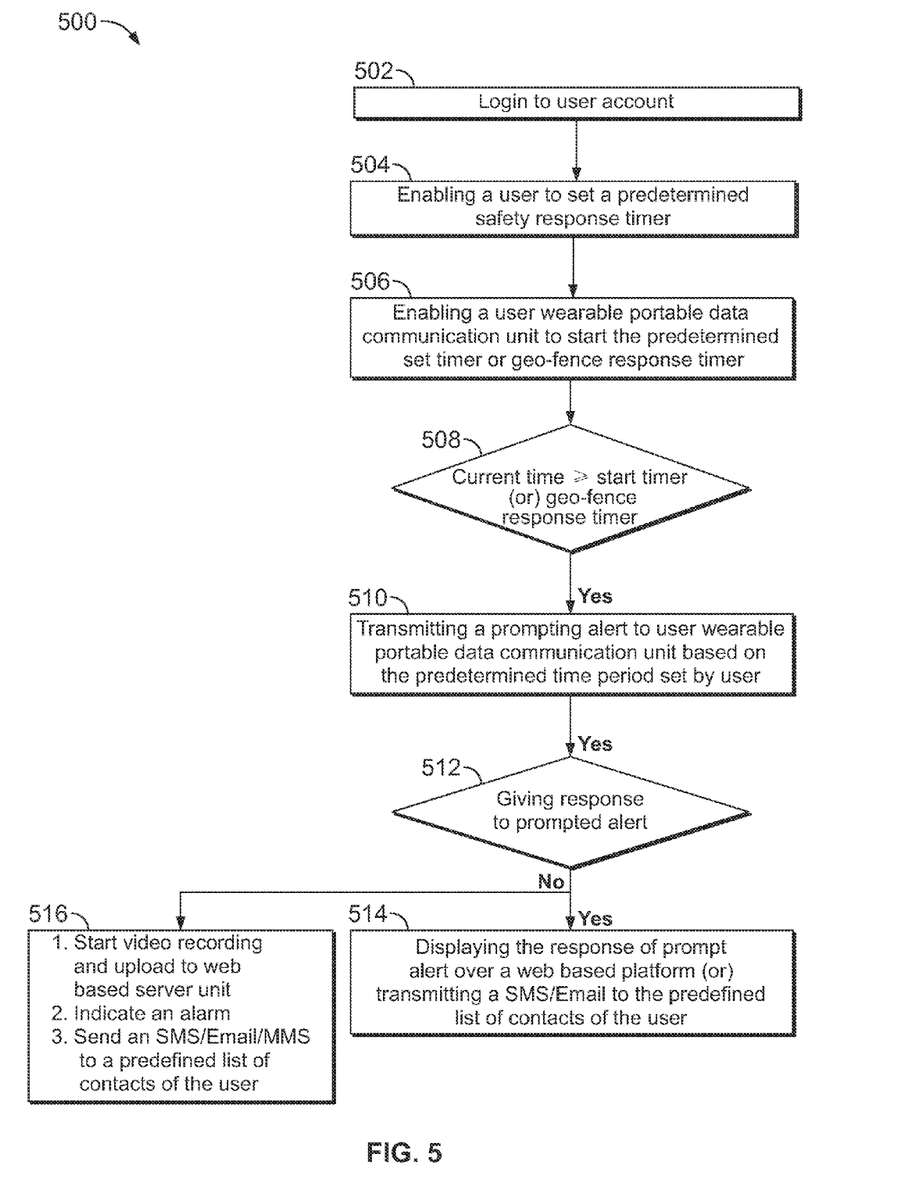
FIG. 5 is a flow diagram illustrating the process of transmitting notification and alerts based on the safety response of the user.

FIG. 5 is a flow diagram 500 illustrating the process of transmitting notification and alerts based on the safety response of the user. According to a non limiting exemplary embodiment of the present disclosure, at 502 the user wearing the user wearable portable data communication unit logins to his/her user registered account through a web based server unit over a portable device or through an application downloaded on the user wearable portable data communication unit. Next at 504 the user is enabled to set a predetermined safety response timer and enable the user wearing the user wearable portable data communication unit to start the predetermined set timer or the geo-fence response time at 506.

Further at 508, the current time is compared with the start timer or the provided geo-fence timer by determining whether the current time is greater then the start time. If the current time is found to be greater than the start time at 508, the method continues with 510 by transmitting a prompting alert to the user wearable portable data communication unit based on the predetermined time period set by the user. Next the response to the prompted alert is determined at 512, if there is a response from the user, the response of the prompted alert is displayed over a web based server unit or transmitted as a short message or email to the predefined list of contacts provided by the user at 514. If there is a lack of response from the user at 512, a video is recorded and uploaded to a web based server unit, an alarm indication is provided, a short message service or email or multimedia message service is transmitted to the predefined list of contacts provided by the user at 516.

Figure 6:
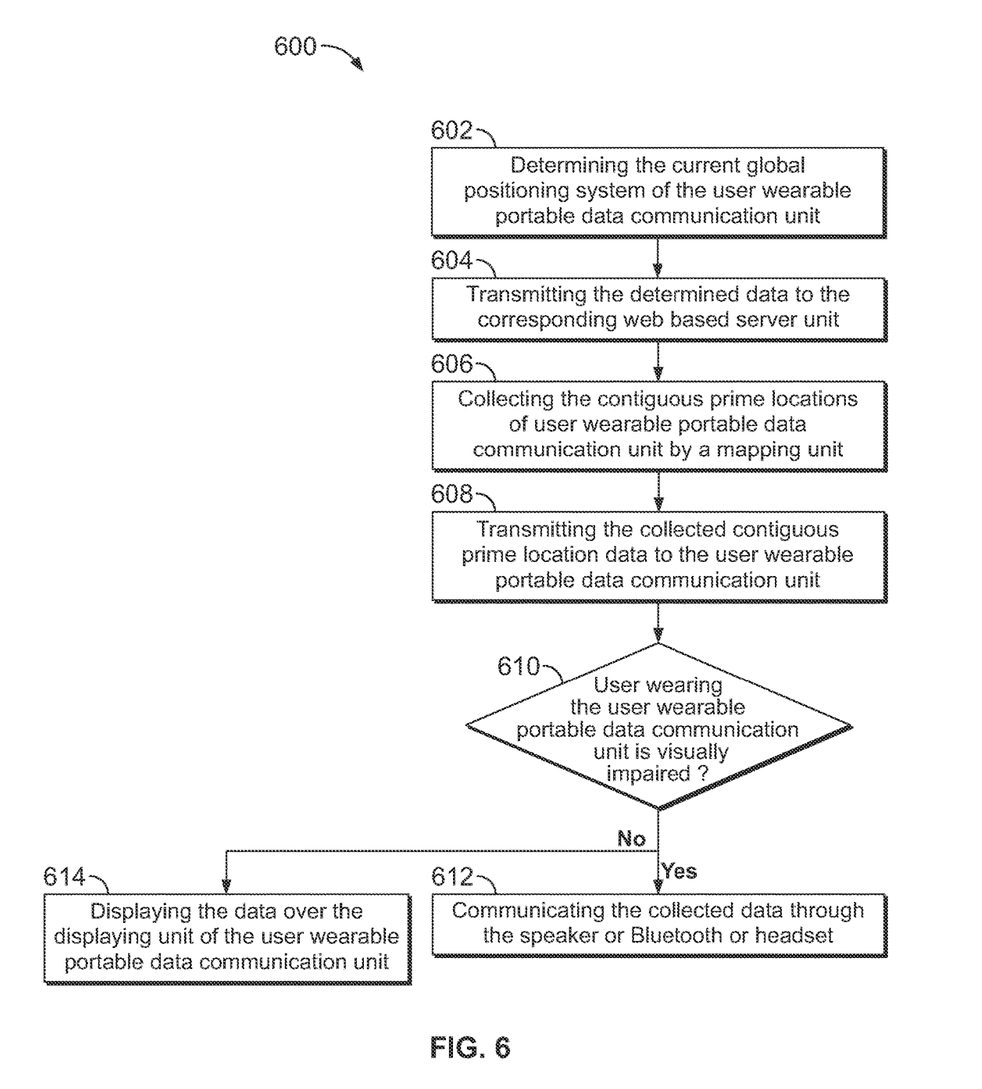
FIG. 6 is a flow diagram illustrating the method for collecting the contiguous prime locations of the user wearing the user wearable portable data communication unit.

FIG. 6 is a flow diagram 600 illustrating the method for collecting the contiguous prime locations of the user wearing the user wearable portable data communication unit. According to a non limiting exemplary embodiment of the present disclosure, at 602 the current global positioning system of the user wearable portable data communication unit is determined and transmitted to a corresponding web based server unit at 604. Further at 606, the contiguous prime location data of the user wearable portable data communication unit is collected by using mapping unit integrated within the user wearable portable data communication unit.

Further at 608, the collected contiguous prime location data is transmitted to the corresponding user wearable portable data communication unit. At 610, the user wearing the user wearable portable data communication unit is determined that whether the user is visually impaired or not. If the user wearing the user wearable portable data communication unit is determined to be visually impaired, the data collected by the user wearable portable data communication unit at 612 are transmitted to the visually impaired user data through a speaker, Bluetooth, headset and the like. If the user is not determined as visually impaired person at 610, the method continuous with 614 by displaying the data collected by the user over the display unit of the user wearing the user wearable portable data communication unit.

While specific embodiments of the invention have been shown and described in detail to illustrate the inventive principles, it will be understood that the invention may be embodied otherwise without departing from such principles.

What is claimed is:

1. A system for transmitting alerts and notifications to a user, the system comprising:

a user wearable portable data communication unit configured to set a predetermined period of time and select a geographical area by using a mapping software integrated with the user wearable portable data communication unit for geo-fencing the selected geographical area;

an alerting unit configured in the user wearable portable data communication unit configured to determine a crossing of the user wearing the user wearable portable data communication unit from the selected geo-fence area and if the predetermined time period set by the user is exceeded, transmits notifications and alerts a predefined list of contacts and the corresponding user wearing the user wearable portable data communication unit; and a web based server unit in communication with the user wearable portable data communication unit through a data communication network configured to store the predefined list of contacts, and each of threshold levels, frequency, way points, current location of the user, and software versions to update the user wearable portable data communication unit with the latest settings when a flag is detected in the response of a http post message consisting of either GPS or sensor data to web server, whereby the latest settings include a global positioning system sampling interval and a data upload interval.

2. The system of claim 1, further comprising a display unit configured in the user wearable portable data communication unit to display the geographical area selected by the user through a mapping software integrated with the user wearable portable data communication unit.

3. A method for transmitting alerts and notifications to a user, the method comprising:

setting a predetermined period of time to a user wearable portable data communication unit by a user, and selecting a geographical area displayed over the user wearable portable data communication unit by using a mapping software, whereby the mapping software is integrated with the user wearable portable data communication unit configured to fence the selected geographical area;

collecting one or more locations contiguous to the current geographical location of the user wearable portable data communication unit by the mapping software based on the current global positioning system of the user wearable portable data communication unit;

transmitting notifications to a predefined list of contacts provided by the user wearing the user wearable portable data communication unit by an alert unit on determining a crossing of the user wearing the user wearable portable data communication unit from the selected geographical area and exceeding the predetermined time period set by the user;

prompting safety response alerts to the user wearing the user wearable potable data communication unit based on the predetermined time period set by the user, whereby the alerts include an alert message and an alarm sound; and dynamically responding back to the prompted alerts by pressing a button configured in the user wearable portable data communication unit for avoiding the transmission of notifications to the predefined list of contacts provided by the user wherein the alerts are transmitted to all of the predefined list of contacts on determining the current geographical location of the user in accordance with the predetermined time period set to the user wearable portable data communication unit if no response is received.

4. The method of claim 3, further comprising a step of polling a web based server unit by the user wearable portable data communication unit through a data communication network for receiving automatic trigger from the web based server unit, a latest firmware version from the web based server unit, an updated version of firmware stored in the web based server unit, and loading it on the user wearable portable data communication unit.

5. The method of claim 4, further comprising a step of storing the updated settings received from the web based server unit in a memory unit configured in the user wearable portable data communication unit to act in accordance with the stored settings.

6. The method of claim 4, further comprising a step of storing the predefined list of contacts, threshold levels, frequency, way points, current location of the user, and software versions in the web based server unit communicating with the user wearable portable data communication unit.

7. The method of claim 3, further comprising a step of transmitting the collected one or more locations contiguous to the current geographical location of the user wearable portable data communication unit worn by a visually impaired person through a speaker, Bluetooth, and radio communication according to the predetermined time period set by the user.

8. A system for transmitting alerts and notifications to a predefined list of contacts, the system comprising:

a user wearable portable data communication unit comprising of a first strap, second strap, the first end of the strap is attached to the first end of the main housing and the second strap attached to the second end of the main housing enabling the user to tie user wearable portable communication device to the wrist of the user;

user wearable portable communication unit configured to set a period of time and select a geographical area by using a mapping software integrated with the user wearable portable data communication unit for geofencing the selected geographical area;

an alerting unit configured in the user wearable portable data communication unit to transmits notifications and alerts to the predefined list of contacts and to the corresponding user wearing the user wearable portable data communication unit either when the user crosses the selected geographical area with the period of time, or when the time that the user spends within the selected geographical area is greater than the set period of time, and wherein the notifications and the alerts are transmitted after the user does not respond by pressing a button on the user wearable portable communication unit to an initial alert that is prompted to the user; and a web based server unit in communication with the user wearable portable data communication unit through a data communication network configured to store the predefined list of contacts, and each of threshold levels, frequency, way points, current location of the user, and software versions to update the user wearable portable data communication unit with the latest settings, whereby the latest settings include a global positioning system sampling interval and a data upload interval.

\* \* \* \* \*